United States Patent
Lee et al.

(10) Patent No.: US 6,184,984 B1
(45) Date of Patent: Feb. 6, 2001

(54) SYSTEM FOR MEASURING POLARIMETRIC SPECTRUM AND OTHER PROPERTIES OF A SAMPLE

(75) Inventors: Shing Lee; Haiming Wang, both of Fremont; Adam Norton, Palo Alto; Mehrdad Nikoonahad, Menlo Park, all of CA (US)

(73) Assignee: Kla-Tencor Corporation, San Jose, CA (US)

(*) Notice: Under 35 U.S.C. 154(b), the term of this patent shall be extended for 0 days.

(21) Appl. No.: 09/246,922

(22) Filed: Feb. 9, 1999

(51) Int. Cl.$^7$ .................................................. G01N 21/21
(52) U.S. Cl. ............................................................ 356/369
(58) Field of Search .................................. 356/365, 366, 356/369, 364, 367, 368, 381, 382; 250/225

(56) References Cited

U.S. PATENT DOCUMENTS

| | | |
|---|---|---|
| 5,042,951 | 8/1991 | Gold et al. . |
| 5,166,752 | 11/1992 | Spanier et al. . |
| 5,181,080 | 1/1993 | Fantom et al. . |
| 5,486,701 | 1/1996 | Norton et al. . |
| 5,596,406 | 1/1997 | Rosencwaig et al. . |
| 5,608,526 | 3/1997 | Piwonka-Corle et al. . |
| 5,747,813 | 5/1998 | Norton et al. . |
| 5,910,842 | * 6/1999 | Piwonka-Corle et al. ........... 356/369 |

OTHER PUBLICATIONS

"Analysis of Semiconductor Surfaces With Very Thin Native Oxide Layers By Combined Immersion And Multiple Angle Of Incidence Ellipsometry," I. Ohlidal et al., *Applied Surface Science*, 35 (1988–89) pp. 259–273.

"Determination Of The "Optical" Thickness And Of The Filling Factor Of Discontinuous Au Films From Photometric And Ellipsometric Measurements," E. Elizalde eta l., *Optics Communications*, vol. 60, No. 6, Dec. 15, 1986, pp. 378–382.

"Variable Angle Spectroscopic Ellipsometry," S.A. Alterovitz et al., *Solid State Technology*, Mar. 1988.

"Application of spectroscopic ellipsometry to complex samples," J. L. Freeouf, *Appl. Phys. Lett.*, 53(24), Dec. 12, 1988, pp. 2426–2428.

"Spectroscopic ellipsometry Studies of SIMOX structures and correlation with cross–section TEM," *Vacuum*, vol. 42, Nos. 5/6, 1991, pp. 359–365.

"Spectroscopic Ellipsometry for the Characterization of Thin Films," F. Ferrieu et al., *J. Electrochem. Soc.*, vol. 137, No. 7, Jul. 1990, pp. 2203–2208.

International Search Report dated Jun. 8, 2000.

* cited by examiner

*Primary Examiner*—Hoa Q. Pham
(74) *Attorney, Agent, or Firm*—Majestic, Parsons, Siebert & Hsue P.C.

(57) ABSTRACT

A polarized sample beam of broadband radiation is focused onto the surface of a sample and the radiation modified by the sample is collected by means of a mirror system in different planes of incidence. The sample beam focused to the sample has a multitude of polarization states. The modified radiation is analyzed with respect to a polarization plane to provide a polarimetric spectrum. Thickness and refractive information may then be derived from the spectrum. Preferably the polarization of the sample beam is altered only by the focusing and the sample, and the analyzing is done with respect to a fixed polarization plane. In the preferred embodiment, the focusing of the sample beam and the collection of the modified radiation are repeated employing two different apertures to detect the presence or absence of a birefringence axis in the sample. In another preferred embodiment, the above-described technique may be combined with ellipsometry for determining the thicknesses and refractive indices of thin films.

90 Claims, 6 Drawing Sheets

SYSTEM FOR MEASURING POLARIMETRIC SPECTRUM AND OTHER PROPERTIES OF A SAMPLE

BACKGROUND OF THE INVENTION

This invention relates in general to non-destructive techniques for measuring surface parameters of samples and, in particular, to a system for measuring polarimetric spectrum and other properties of a sample.

For a number of industrial applications, it is useful to determine sample surface parameters such as thicknesses of thin films and their refractive indices. These parameters may be determined by a number of techniques. Among the better known non-destructive testing techniques are those of spectroreflectometry and spectroscopic ellipsometry.

In spectroreflectometry, an incident radiation beam reflects from a sample, and the intensity of the reflected radiation is analyzed to determine properties of the sample. The incident radiation may include multiple frequency components so that a spectrum of measured data (known as the reflectance spectrum or relative reflectance spectrum) is measured. U.S. Pat. No. 5,747,813 describes a type of broadband spectroreflectometer; this patent is incorporated herein in its entirety by reference.

A spectroscopic ellipsometer is described in U.S. Pat. No. 5,608,526, which is incorporated herein in its entirety by reference. As described in this patent, an incident radiation beam having a known polarization state is reflected from a sample, generally at a large angle of incidence and the polarization of the reflected radiation is analyzed to determine properties of the sample. The polarization of the reflected radiation is altered from that of the incident beam so that the change of polarization state in amplitude and phase is measured to determine the thicknesses and refractive indices of thin films on the surface of the sample.

Spectroreflectometry is simpler and less expensive than spectroscopic ellipsometry, but spectroscopic ellipsometry is more accurate and sensitive to surface properties than spectroreflectometry. While spectroreflectometry and spectroscopic ellipsometry are useful non-destructive testing techniques, it may be difficult to use such techniques to measure certain surface parameters, such as surface birefringence.

It is therefore desirable to provide an improved measurement system for measuring sample parameters such as birefringence. It may also be desirable to provide a polarimeter system for measuring properties of the sample surface to supplement the above-described non-destructive testing techniques.

SUMMARY OF THE INVENTION

The polarimetry system proposed by Applicants retains the simplicity of the spectroreflectometer but is as sensitive to surface properties as the spectroscopic ellipsometer. A polarized sample beam of broadband radiation is focused onto the surface of a sample and the radiation modified by the sample is collected. The sample beam focused to the sample has a multitude of polarization states. The radiation modified by the sample is analyzed with respect to a polarization plane to provide a polarimetric spectrum. Thickness and refractive index information may then be derived from the spectrum. Preferably the polarization of the sample beam is altered only by the focusing and by the sample, and the analyzing is done with respect to a fixed polarization plane.

In the preferred embodiment, the focusing of the sample beam and the collection of the modified radiation are repeated employing two different apertures to detect the presence or absence of a birefringence axis in the sample. In another preferred embodiment, the above-described technique may be combined with ellipsometry for determining the thicknesses and refractive indices of thin films.

BRIEF DESCRIPTION OF THE DRAWINGS

For simplicity in description, identical components are identified by the same numerals.

DESCRIPTION OF THE PREFERRED EMBODIMENTS

Figure 1:
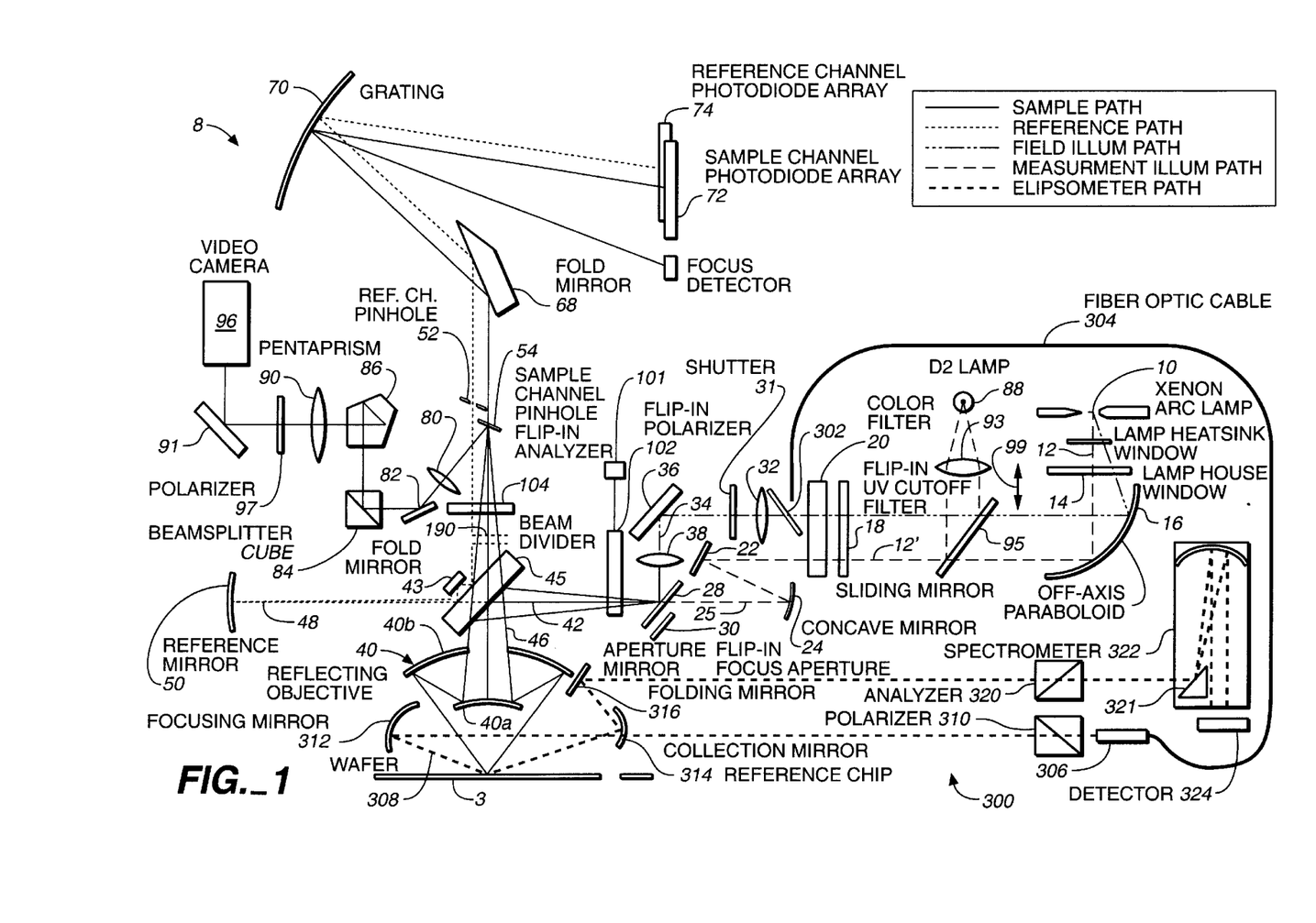
FIG. 1 is a schematic view of a combined instrument including a spectroscopic ellipsometer and a polarimetric system to illustrate the preferred embodiment of the invention.

FIG. 1 is a schematic view of a combined instrument including a spectroscopic ellipsometer and a polarimetric system to illustrate the preferred embodiment of the invention. Before the spectroscopic ellipsometer of the combined instrument is discussed, the polarimetric system 8 is first described in some detail in reference to FIGS. 1 and 2. As indicated below, while preferably system 8 is advantageously used together with a spectroscopic (or single wavelength) ellipsometer as in the combined instrument of FIG. 1, this system can also be advantageously used by itself for measuring samples.

The overall optical arrangement in polarimetric system 8 resembles the spectroreflectometer described in U.S. Pat. No. 5,747,813 and retains its simplicity. However, different from such spectroreflectometer, system 8 of this invention measures polarimetric reflectance spectrum rather than polarization insensitive reflectance spectrum as in the system of U.S. Pat. No. 5,747,813. System 8 is therefore more sensitive to surface properties than the system of U.S. Pat. No. 5,747,813. While in the preferred embodiment, the invention is illustrated as detecting radiation reflected by the sample, it will be understood that the invention will function essentially as described herein where radiation transmitted by the sample is detected instead; such and other variations are within the scope of the invention. For simplicity, the preferred embodiment will be described below as measuring the reflected radiation, with the understanding that such description can be readily extended to measure the transmitted radiation.

The convention for showing the sample path, reference path, field illumination path, measurement illumination path and ellipsometer path are shown in the upper right-hand corner of FIG. 1. As noted above, the overall optical arrangement in the system for measuring polarimetric parameters is described below in reference to FIGS. 1 and 2.

Figure 2:
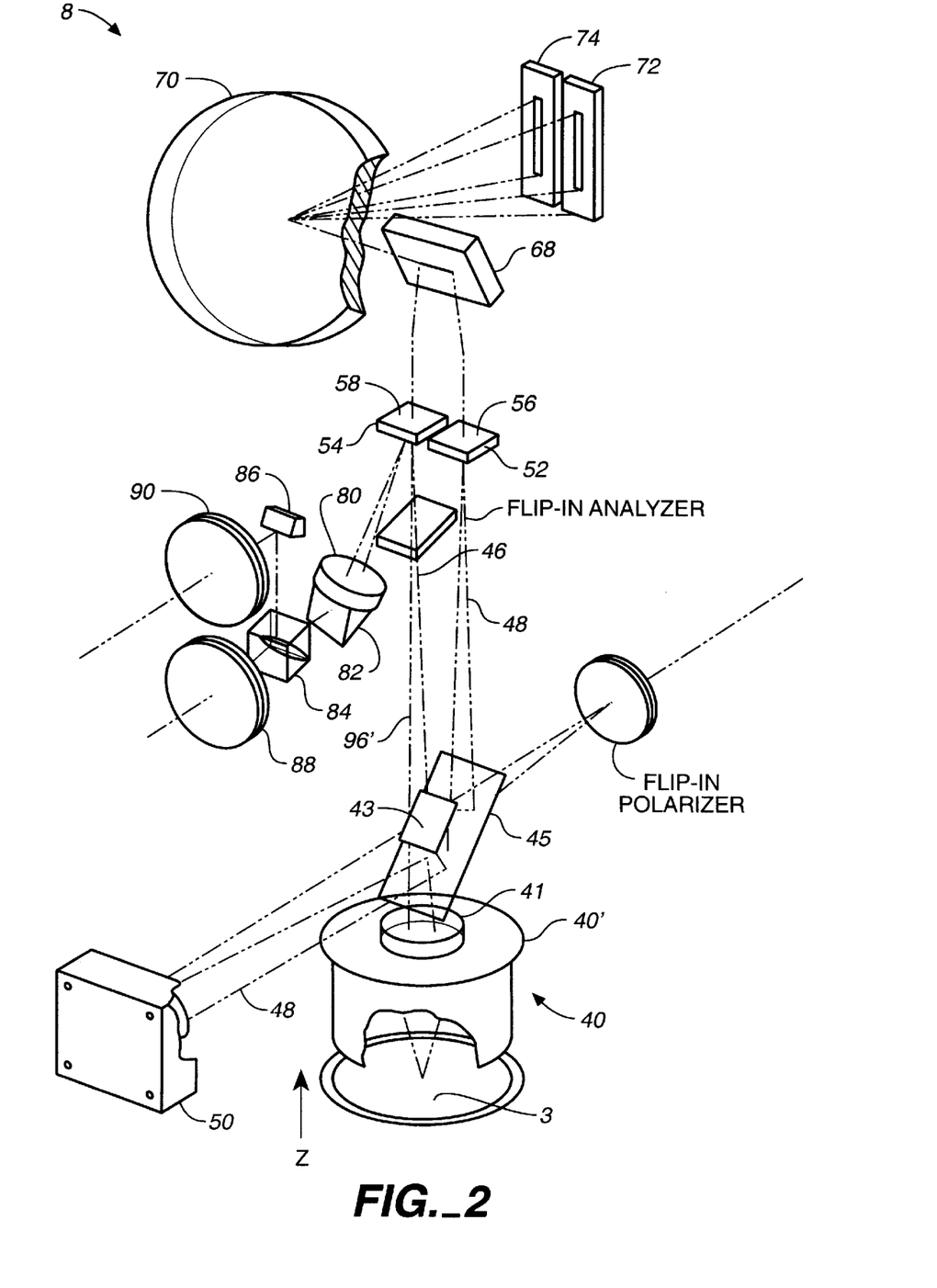
FIG. 2 is a perspective view of the polarimetric system of FIG. 1.

Each of FIGS. 1 and 2 shows the same embodiment of an optical system according to the present invention for measuring polarimetric parameters. Part of the focusing and other optical elements of system 8 and the spectroscopic ellipsometer of FIG. 1 are omitted in FIG. 2 to simplify the figure The elements are explained below in conjunction with the figure which most clearly shows their placement with respect to other elements. Referring to FIG. 1, an optical system 8 for measuring the relative reflectance spectrum of a wafer 3 includes an illumination subsystem, a reflectometer subsystem, a viewing subsystem and an autofocus subsystem, wherein any given optical element may be part of more than one subsystem. The illumination subsystem includes a lamp 10, such as a xenon arc lamp, which emits a light beam 12 of visible and/or ultraviolet (UV) light, a lamp housing window 14, an off-axis paraboloidal mirror 16, a flip-in UV cutoff filter 18, a color filter wheel 20, a flat mirror 22, a concave mirror 24, an aperture mirror 28 with a flip-in 40 $\mu$m fine focus aperture 30, a large achromat 32, a field illumination shutter 31, a fold mirror 36, and a small achromat 38. In FIG. 2, objective 40 includes mirrors and a housing 40' enclosing mirrors 40a, 40b, but leave sufficient spacing between the housing and the wafer for the oblique illumination beam from the spectroscopic ellipsometer (not shown in FIG. 2).

The illumination system provides a combined beam 42 comprising a measurement beam 25 and a field illumination beam 34. Lamp 10 emits light beam 12 through a lamp housing window 14. The lamp housing window is not necessary for optical reasons; however it is provided to contain lamp 10 should the lamp crack and explode. A xenon lamp is preferred over other lamps such as tungsten or deuterium lamps, because a xenon lamp will give a flatter output covering a spectrum from UV to near infrared. To provide a sample beam having components of wavelengths in a range including 190–220 nm, an additional deuterium lamp 88 is used in combination with the xenon lamp 10 to cover a broader spectrum that includes the deep UV. By using the two lamps together, the resulting combined spectrum of radiation supplied for detecting samples can be extended to a range of about 190 to 800 or 830 nm. Extending the spectrum to the deep UV range is useful for photolithography. Radiation from lamp 88 is focused by lens 93 and reflected by mirror 95 to filter 18 and combined with the radiation from the lamp 10 to form the combined beam 12'. By moving mirror 95 into or out of the path of beam 12 along arrow 99, it is possible to include or exclude radiation from the deuterium lamp 88 from the measurement beam 25.

Off-axis paraboloid mirror 16 collimates light beam 12, which after combination with the radiation from the lamp 88 to form beam 12', can be optionally filtered by flip-in UV cutoff filter 18 and color filter wheel 20. Flip-in UV cutoff filter 18 is used in part to limit the spectrum of light beam 12', so that when light beam 12' is dispersed by a diffraction grating, the first and second order diffraction beams do not overlap. Part of light beam 12' is reflected by flat mirror 22 onto concave mirror 24 to form measurement beam 25. Concave mirror 24 focuses measurement beam 25 onto the aperture in aperture mirror 28.

Another part of light beam 12, field illumination beam 34, is focused by large achromat 32 near fold mirror 36, causing fold mirror 36 to reflect an image of lamps 10, 88 toward small achromat 38. Small achromat 38 collects the light in field illumination beam 34 before the light reflects off aperture mirror 28. Aperture mirror 28 is a fused silica plate with a reflective coating on one side, with a 150 $\mu$m square etched from the reflective coating to provide an aperture for measurement beam 25. The aperture is placed at one conjugate of an objective 40. The field illumination can be turned off by placing field illumination shutter 31 in the optical path of field illumination beam 34.

The narrow measurement beam 25 and wide field illumination beam 34 are rejoined at aperture mirror 28, with field illumination beam 34 reflecting off the front of aperture mirror 28, measurement beam 25 passing through the aperture and polarizer 102, which may be moved into or out of the path of beam 25 by a motor 101.

FIG. 1 shows the reflectometer, viewing and autofocus subsystems of optical system 8, including objective 40, a beam divider mirror 45, a sample beam 46, an optional reference team 48, a concave mirror 50, a flat mirror 43, a reference plate 52 with a reference spectrometer pinhole 56, a sample plate 54 with a sample spectrometer pinhole 58, a second fold mirror 68, a diffraction grating 70, a sample linear photodiode array 72, a reference linear photodiode array 74, an achromat 80 with a short focal length, mirror 82, a beamsplitter cube 84, a penta prism 86, achromat 90 with long focal lengths, a neutral density filter wheel 97, a third fold mirror 91, and avideo camera 96. Some of these components are not shown in FIG. 2, for clarity.

Several magnifications are possible for objective 40. In one embodiment, a Schwarzchild design all-reflective objective may be mounted on a rotatable turret which allows for one of several different objectives (not shown) to be placed in the optical path of sample beam 46. It is possible to include a refractive element of low power in the optical path of sample beam 46 without significantly affecting the measurements in this invention.

The measurement of the relative reflectance spectra of wafer 3 will now be described. When field illumination shutter 31 is placed in the path of field illumination beam 34, combined beam 42 comprises only measurement beam 25. Combined beam 42 is split by beam divider mirror 45, a totally reflecting mirror placed so as to deflect half of combined beam 42 towards objective 40, thus forming sample beam 46, the undeflected half of combined beam 42 forming reference beam 48. Because sample beam 46 and optional reference beam 48 are derived from the same source, lamps 10 and 88, and because combined beam 42 is radially uniform, reference beam 48 and sample beam 46 have proportionally dependent spectral intensities. Furthermore, since beam divider mirror 45 is a totally reflecting mirror in half of an optical path rather than a partially reflecting mirror in the entire optical path, a continuous broadband spectrum is reflected with good brightness.

Reference beam 48 does not initially interact with beam divider mirror 45, but instead illuminates concave mirror 50. Concave mirror 50 is slightly off-axis, so that reference beam 48 is reflected onto the reverse face of beam divider mirror 45, where flat mirror 43 re-reflects reference beam 48 into alignment with reference spectrometer pinhole 56. Flat mirror 43 is provided to realign reference beam 48 with sample beam 46 so that both beams pass through their respective spectrometer pinholes substantially parallel. This allows for simpler alignment of the spectrometer element for both channels, since the reference beam enters the spectrometer parallel to the sample beam.

Since reference beam 48 does not interact with the surface of beam divider mirror 45 which reflects beam 46, there is no loss in reference intensity as reference beam 48 passed beam divider mirror 45. While reference beam 48 does interact with a mirror 43 on the reverse side of beam divider mirror 45, these two mirrors are independent, since no light passed through beam divider mirror 45. Indeed, in an alternative embodiment where the two reflecting surfaces of beam divider mirror 45 cannot easily be placed together on one optical element, the reflecting surfaces exist on separate mirror elements.

The focal length of concave mirror 50 is such that reference beam 48 is in focus at reference spectrometer pinhole 56. The light passing through reference spectrometer pinhole 56 and reflecting off fold mirror 68 is dispersed by diffraction grating 70. The resulting first order diffraction beam is collected by reference linear photodiode array 74, thereby measuring a relative reference spectrum.

Polarized sample beam 46 is reflected off beam divider mirror 45 towards objective 40, where sample beam 46 is focused onto wafer 3, and the reflected sample beam 46' is focused by objective 40 onto sample spectrometer pinhole 58. The reflected sample beam 46' does not interact with beam divider mirror 45 on the reflected path, because reflected sample beam 46' passed through the space behind beam divider mirror 45, where reference beam 48 also passes. The radiation from reflected sample beam 46' from the sample 3 passes through an analyzer 104 before it reaches pinhole 58. The light passing through sample spectrometer pinhole 58 and reflecting off fold mirror 68 is dispersed by diffraction grating 70 according to wavelength of the light. As with the reference beam, the resulting first order diffraction beam of the sample beam is collected by sample linear photodiode array 72, thereby measuring the sample polarimetric spectrum. Because the two beams cross at diffraction grating 70, the photodiode array apparently aligned with sample beam 46 in FIG. 2 is in fact the photodiode array for reference beam 48, and vice versa. The polarizer 102 and analyzer 104 do not rotate and are preferably stationary. Analyzer 104 therefore analyzes the radiation modified by the sample and collected by objective 40 according to a fixed plane of polarization.

The relative reflectance spectrum can then be simply obtained by dividing the sample light intensity at each wavelength by the relative reference intensity at each wavelength. Typically, this might involve 512 division computations, where 512-diode linear photodiode arrays are used to record the sample and reference spectra. In the preferred embodiment, the spectrum ranges from about 190 nm to 800 or 830 nm.

In one embodiment of the present invention, diffraction grating 70 is a concave holographic grating and the spectrometer pinholes are 15 mm apart. The diffraction grating is holographically corrected to image multiple spectra, since the 15 mm spacing does not allow for both beams to be centered on the grating. One such grating is a multiple spectra imaging grating supplied by Instruments S.A. Also, the grating is designed so that the angle of the detector causes reflections off the detector to fall away from the grating.

Combined beam 42, which may include field illumination, is reflected off beam divider mirror 45 toward wafer 3. When reflectance spectra measurements and autofocusing are being performed, the field illumination is off to minimize scattered light.

Because of the innovative arrangement of optical elements used to measure relative reflectance spectra, many of the elements of in the spectra measurement subsystem are also used in the autofocus subsystem. For example, since relative reflectance spectrum measurement in the embodiment shown in the figures uses beam divider mirror 45 as opposed to a partially reflecting mirror, the resulting beam reflected from the wafer 3 has a circularly asymmetric cross section. This allows for detecting the direction of focus as well as the relative distance to move objective 40 or wafer 3 to achieve an in-focus condition, whereas with a circularly symmetric cross section, the direction of focus cannot be detected.

Figure 3A:
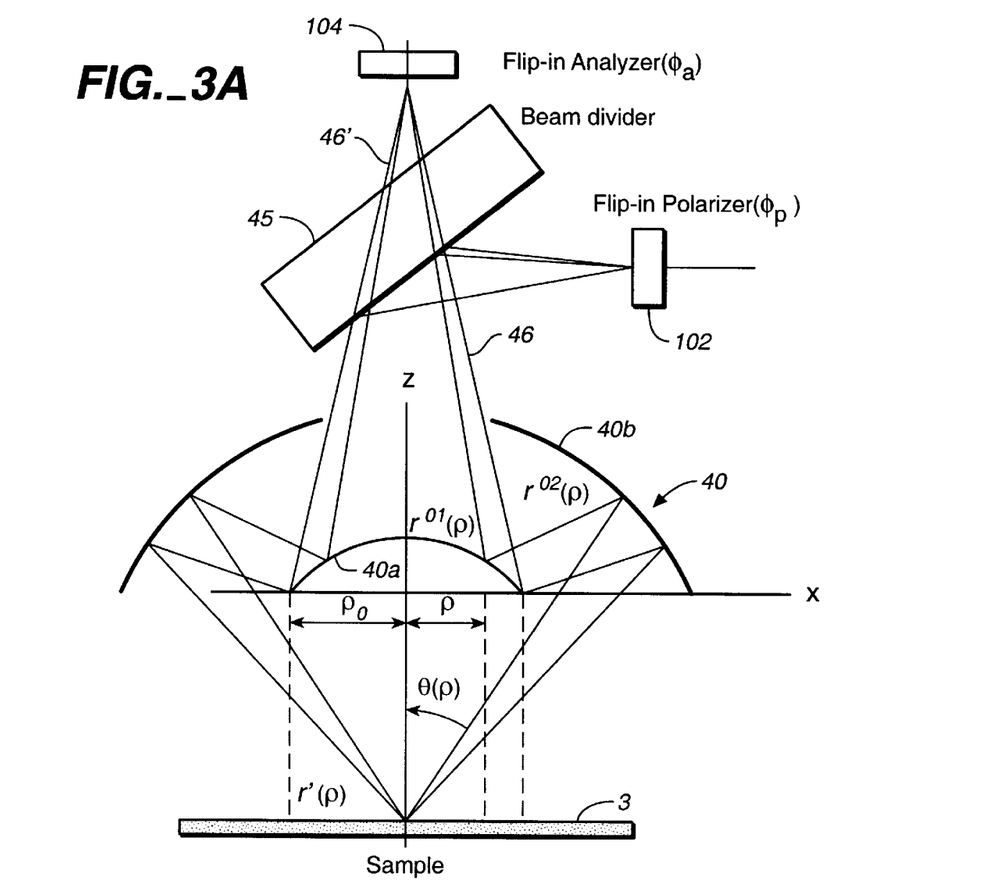
FIG. 3A is a simplified schematic view of a portion of the system of FIG. 1 for measuring polarimetric parameters.
Figure 3B:
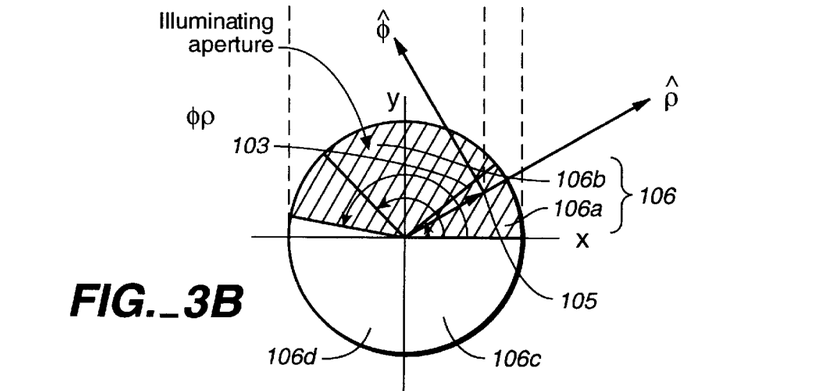
FIG. 3B is a graphical illustration of the illuminating aperture of FIG. 2A.

The polarimetric system 8 in FIGS. 1 and 2 differs from that described in U.S. Pat. No. 5,747,813 in that the sample beam 46 is polarized in the system of this application. Thus, when the sample beam 46 is reflected by objective 40 towards the sample 3, the beam that is focused onto the wafer has a multitude or a plurality of different polarization states. This is illustrated more clearly in reference to FIGS. 3A, 3B. Sample beam 46 is reflected by mirror 40a towards mirror 40b which then focuses the beam towards the sample 3 as shown in FIG. 3A. FIG. 3B is a schematic view of the illumination aperture of the sample beam 46 when focused onto the wafer 3. The various quantities in FIGS. 3A, 3B are defined by reference to cylindrical coordinates $\rho$, $\phi$ and $\theta$, where $\rho$ is the radius of a point (distance to the origin) in the coordinate system, $\phi$ the angle of a plane normal to the sample surface containing the point to a reference plane normal to the surface of the sample, and $\theta$ the angle from the normal to the sample surface of a line connecting the point to the origin (angle of incidence to the normal).

In reference to FIG. 3A, it is assumed that polarizer 102 has a plane of polarization defined by the plane at $\phi_p$, so that the sample beam 46 that emerges from the polarizer and reflected by beam divider 45 also has this polarization. When beam 46 is reflected first by mirror 40a and then by mirror 40b which focuses the beam onto the sample 3, the beam that is focused onto the sample 3 arrive in different planes of incidence as illustrated in FIGS. 3A, 3B. In FIG. 3B, the plane of polarization $\phi_p$ of the beam 46 is indicated at 103.

From the description above, beam divider mirror 45 deflects about half of the polarized beam to become the sample beam 46 and passes the remaining half of the beam as the reference beam 48. For this reason, the illumination aperture (shaded area 106) in FIG. 3B appears to be approximately semicircular in shape. Thus the radiation that is focused onto sample 3 by objective 40 will be incident onto the sample at planes of incident that span the semicircular area. The radiation incident on the wafer in one plane of incidence at one value of the angle $\phi$ in the area will have s- and p-polarizations that are different from those of radiation in a different plane of incidence having a different value of the angle $\phi$ in the area. The s- and p-polarizations of radiation in different planes of incidence will, by definition, have different orientations, so that the polarization state of the incident radiation in one plane of incidence will be different from that of the incident radiation in a different plane of incidence. Therefore, the radiation incident upon sample 3 will have a multitude or plurality of polarization states as a function of $\phi$.

The beam that is focused onto sample 3 will be reduced in intensity compared to sample beam 46 as a function of the combined reflection coefficients of the objectives 40a, 40b as explained below. The radiation originating from sample beam 46 and focused onto the sample by objective 40 is reflected by the sample which again reduces the intensity and changes the phase of each polarization component as a function of the reflection coefficients of the sample. Such radiation is again reflected by objective 40 through a beam divider 45 and analyzer 104 to the spectrometer as described above. While in the preferred embodiment, the same objective used for focusing the radiation onto the sample is also used for collecting the reflected radiation towards the analyzer and spectrometer; it will be understood that this is not required, and a different collection objective may be used in addition to the focusing objective; such and other variations are within the scope of the invention.

Consider the radiation incident from point 105 with coordinates $(\rho, \phi)$ of FIG. 3A in the semicircular illumination aperture with the polarization along the $\phi_p$ direction towards the origin on the sample surface. The electric field can be decomposed in the s- and p-polarizations shown in FIGS. 3A, 3B as follows:

$$\vec{E}_{in} = E_0 \hat{p}_p = E_s^{in} \hat{\phi} + E_p^{in} (-\hat{\rho})$$

$$E_s^{in} = E_s^{in} \hat{p}_p \cdot \hat{\phi} = E_0 \sin(\phi_p - \phi)$$

$$E_p^{in} = E_0 \hat{p}_p \cdot (-\hat{\rho}) = -E_0 \cos(\phi_p - \phi)$$

where $E_{in}$ is the electric field of the radiation in beam 46 after being polarized by the polarizer 102, $E_0$ its amplitude, and $E_s^{in}$, $E_p^{in}$ the components of the radiation along the s- and p-polarizations. After the radiation exits the objective, $$\vec{E}_{out} = E_s^{out} \hat{\phi} + E_p^{out} (-\hat{\rho})$$

$$E_s^{out} = E_0 r_s^o r_s^s \sin(\phi_p - \phi)$$

$$E_p^{out} = -E_0 r_p^o r_p^s \cos(\phi_p - \phi)$$

where $E_{out}$ is the electric field of the radiation in beam 46 after being reflected by the sample 3, and $E_s^{out}$, $E_p^{out}$ its components along the s- and p-polarizations; and where $$r_s^s(r_s^o) \text{ and } r_p^s(r_p^o)$$

are the reflection coefficients for the s- and p-polarizations for the sample (objective). The reflection coefficients for the objective are the product of the reflection coefficients of the two mirrors as shown in FIG. 3A, i.e., $$r_s^o = r_s^{o1} r_s^{o2} \text{ and } r_p^o = r_p^{o1} r_p^{o2}.$$

The electric field at the spectrometer after passing through the analyzer with polarization plane at $\phi_a$ will be along $\hat{P}_a$ can be obtained:

$$\vec{E}_{spectrometer} = E_0 r_s^o r_s^s \sin(\phi_p - \phi) \sin(\phi_a - \phi)$$

$$\left[ 1 + \frac{r_p^o r_p^s}{r_s^o r_s^s} \cot(\phi_p - \phi) \cot(\phi_a - \phi) \right] \hat{P}_a$$

The detector current can be expressed as $$I_{det} \propto \int_0^{\phi_o} \int_0^{\rho_o} \rho \, d\rho \, d\phi |E_{spectrometer}|^2 \qquad (1)$$

If the polarizer 102 is omitted, then the detector current for semicircular apertures becomes $$I_{det} \propto \frac{1}{2} |E_0|^2 [R_s^o R_s^s + R_p^o R_p^s] \qquad (2)$$

In equation (2), $$R_s^o, R_s^s, R_p^o, R_p^s$$

are defined respectively as $$|r_s^o|^2, |r_s^s|^2, |r_p^o|^2, |r_p^s|^2.$$

One must keep in mind that $$r_s^o, r_s^s, r_p^o \text{ and } r_p^s$$

are functions of the angle of incidence, i.e., functions of $\rho$. Where polarize 102 is in place as shown in FIGS. 1–3, a general equation can be derived where the intensity at the spectrometer is a function of the s- and p-reflectivities of the sample and of the objectives and of $\Delta^o$, $\Delta^s$ which are defined by the equations $$r_p^o / r_s^o = \tan \psi^o e^{j\Delta^o},$$

$$r_p^s / r_s^s = \tan \psi^s e^{j\Delta^s}$$

where $$r_p^s, r_s^s$$

are the complex reflection coefficients of the sample surface of radiation at p- and s-polarizations and where $r_p^o$, $r_s^o$ are the complex reflection coefficients of the objectives of radiation at p- and s-polarizations), where $\psi^o$, $\psi^s$, $\Delta^o$ and $\Delta^s$ are also the ellipsometric parameters. Therefore, system 8 is polarization sensitive.

Shown below are some special cases:

A. $\phi = \pi$ \qquad (3)

$$I_{det} \propto \int_0^{\rho_o} \rho \, d\rho |E_0|^2$$

$$\left[ R_s^o R_s^s \left( \frac{\pi}{4} + \frac{\pi}{8} \cos(2\phi_p - 2\phi_a) \right) + R_p^o R_p^s \left( \frac{\pi}{4} + \frac{\pi}{8} \cos(2\phi_p - 2\phi_a) \right) + \frac{\pi}{4} \cos(2\phi_p - 2\phi_a) \sqrt{R_s^o R_s^s R_p^o R_p^s} \cos(\Delta^o + \Delta^s) \right]$$

For the system to be sensitive to the change in $\Delta$, $2(\phi_p - \phi_a) = m\pi$. If $\phi_p = \phi_a$, $$I_{det} \propto \frac{\pi}{8} \int_0^{\rho_o} \rho \, d\rho |E_0|^2 \left[ 3R_s^o R_s^s + 3R_p^o R_p^s + 2\sqrt{R_s^o R_s^s R_p^o R_p^s} \cos(\Delta^o + \Delta^s) \right] \quad (4)$$

$B.\phi_0 = \pi/2$ (5)

$$I_{det} \propto \frac{\pi}{8} \int_0^{\rho_o} \rho \, d\rho |E_0|^2$$

$$\left[ \begin{array}{l} R_s^o R_s^s \left( \dfrac{\pi}{4} + \dfrac{\pi}{8} \cos(2\phi_P - 2\phi_a) - \dfrac{1}{4}\sin(2\phi_P) - \dfrac{1}{4}\sin(2\phi_P) \right) + \\ R_p^o R_p^s \left( \dfrac{\pi}{4} + \dfrac{\pi}{8} \cos(2\phi_P - 2\phi_a) + \dfrac{1}{4}\sin(2\phi_P) + \dfrac{1}{4}\sin(2\phi_P) \right) + \dfrac{\pi}{8}\cos(2\phi_P - 2\phi_a)\sqrt{R_s^o R_s^s R_p^o R_p^s} \cos(\Delta^o + \Delta^s) \end{array} \right]$$

If $\phi_P = \phi_a = \pi/2$, (6)

$$I_{det} \propto \frac{\pi}{8} \int_0^{\rho_o} \rho \, d\rho |E_0|^2 \left[ R_s^o R_s^s \left( \frac{3\pi}{8} - \frac{1}{2} \right) + R_p^o R_p^s \left( \frac{3\pi}{8} + \frac{1}{2} \right) + \frac{\pi}{8} \sqrt{R_s^o R_s^s R_p^o R_p^s} \cos(\Delta^o + \Delta^s) \right]$$

Figure 4:
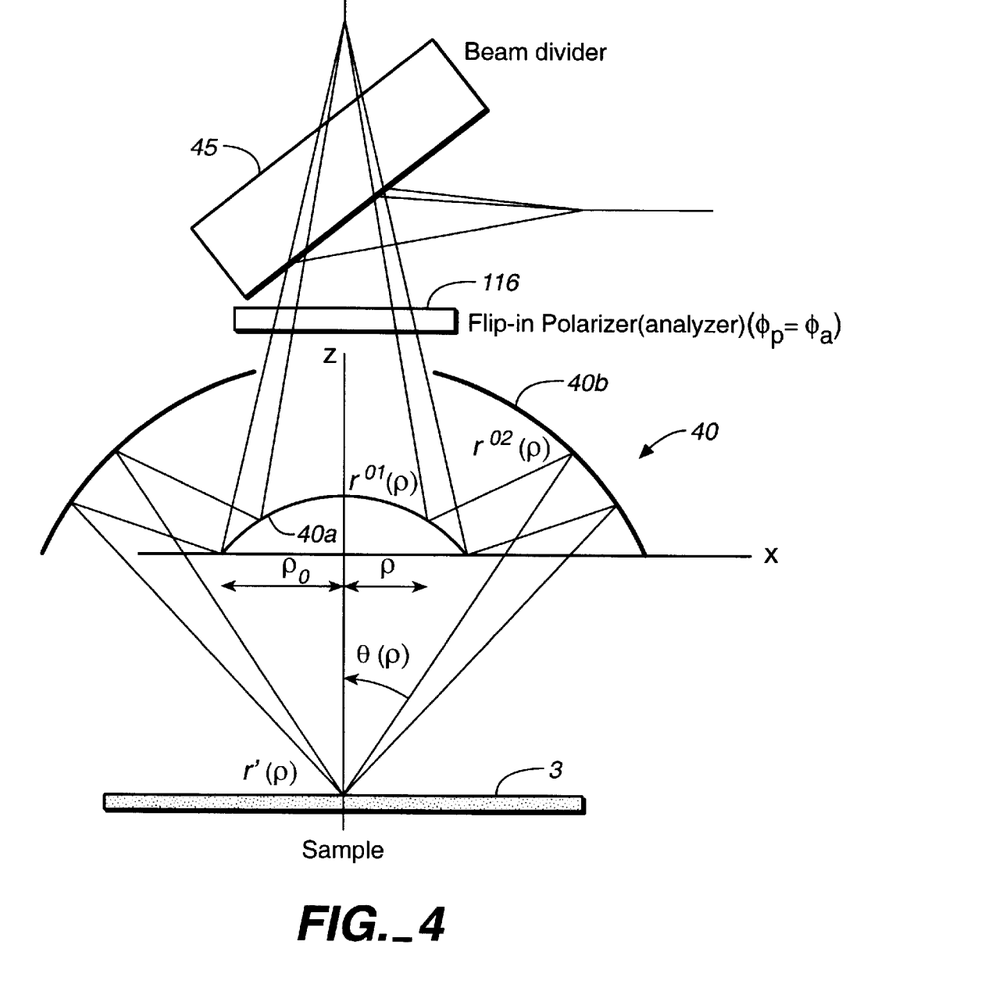
FIG. 4 is a simplified schematic view of a portion of a system for measuring polarimetric parameters to illustrate an alternative embodiment of the invention.

From the above analysis, the $\cos(\Delta^o+\Delta^s)$ Coefficients in the third term in equations (4) and (6) are the largest when the polarizer and analyzer angles are the same, that is, when the polarizer 102 and the analyzer 104 have substantially the same plane of polarization. In other words, we can use a single polarizer to act both as the polarizer and analyzer as shown in FIG. 4. As shown in FIG. 4, the polarizer 116 may be used to replace the polarizer 102 and analyzer 104. The sample channel of the photodiode array will be proportional to equation (5). In this configuration, only one polarizer is needed, and the polarizer and analyzer are self-aligned. As yet another alternative, the polarizer 102 and analyzer 104 may be omitted altogether if the divider 45 is a polarizing beam splitter. For improved sensitivity of film thickness detection, a waveplate or other retarder element 190 shown in dotted line may be inserted between the beam divider 45 and analyzer 104 in FIG. 1, to introduce a phase shift in the argument of cosine coefficients $\cos(\Delta^o+^s)$ in the third term in equations (4) and (6). Preferably, the phase shift in the collected radiation caused by the element 190 prior to analyzing and dispersion is about π4. The thickness of the mirror coating of the mirrors 40a, 40b may also be selected to enhance sensitivity in detection of thicknesses of thin films so that the total change in phase in the radiation focused and collected by the mirrors 40a, 40b is about π/2. This will then cause $\Delta^o$ to be π/2 in the argument of cosine coefficients $\cos(\Delta^o+\Delta^s)$ in the third term in equations (4) and (6), so that the cosine term in these equations converts to a sine term.

The polarimetric spectrum measured in terms of the detector currents in array 72 may be used for deriving useful information about the sample 3. For example, if the types of materials in a number of different layers on sample 3 are known so that one can estimate their refractive indices, such detector currents may be adequate for deriving the thicknesses and accurate refractive indices of the layers. Methods for such derivation is known to those skilled in the art and need not be discussed in detail here. Alternatively, the detector signals may be combined with ellipsometry measurements for deriving film thicknesses and refractive indices. Using broadband radiation for detection in the polarimetric system is advantageous, since one can obtain data points at a number of different wavelengths. Such wealth of data points is very useful for determining the thicknesses and refractive indices of multiple layers on the sample, and may permit one to apply more accurate curve fitting algorithms or to cross-check the accuracy of the measurements.

Figure 5A:
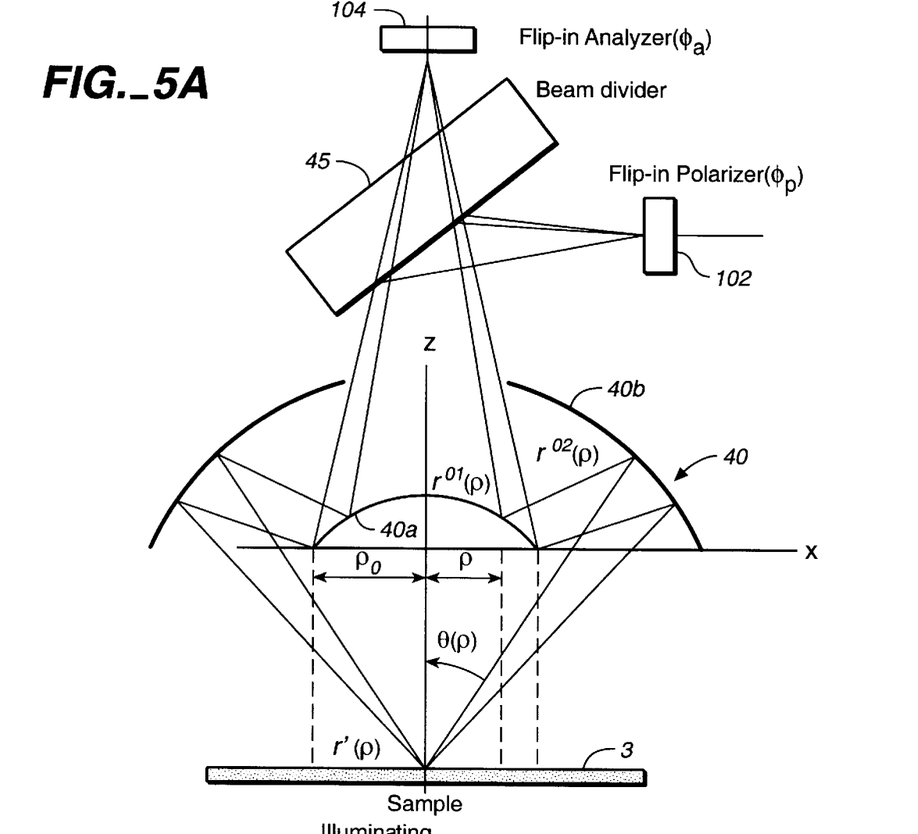
FIG. 5A is a simplified schematic view of the system for measuring polarimetric parameters of FIG. 1 where the optical path of the illumination beam or the reflected beam is passed through an aperture to illustrate the preferred embodiment of the invention.
Figure 5B:
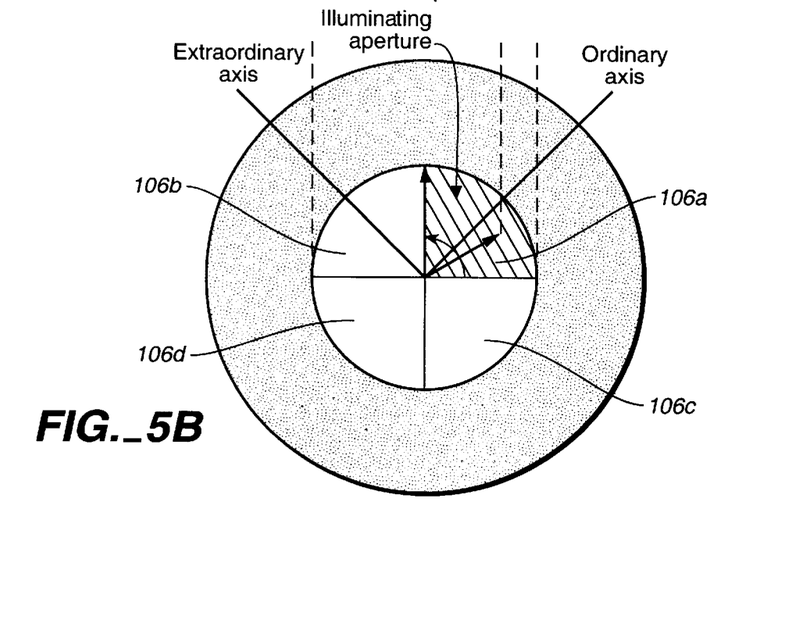
FIG. 5B is a schematic view of the aperture of FIG. 5A relative to axes of birefringence of the sample to illustrate the invention.

The system 8 can also be used to analyze in-plane birefringence samples through two measurements, each with one of the two quadrants of the illumination aperture covered. As shown in FIG. 3B, the illumination aperture is substantially semicircular and contains the first and fourth quadrants 106a, 106b. FIGS. 5A, 5B show illumination only through the first quadrant (shaded area), and the reflection of the illumination beam passes through only the third quadrant 106d. When the first quadrant is covered and the fourth quadrant not covered, a second measurement is then performed with the illumination through the fourth quadrant, and reflection through the second quadrant is collected and measured in a similar manner. This is effectively the same as physically rotating the wafer 3 by 90 degree. Because the axes of birefringence line up differently with the planes of incidence for first and fourth quadrant illumination, the birefringence effects can be deduced from the two successive measurements. If the locations of axes of birefringence with respect to the wafer are known, the measurement can be optimized by orienting the locations of the four quadrants so that the first and the fourth quadrants 106a, 106b are centered about corresponding axes of birefringence, such as about the ordinary and extraordinary axes respectively. As shown in FIG. 5B, where the fourth quadrant of the polarizer 102 is covered and it is assumed that the polarization axis 103 of the polarizer 102 is aligned with the axis of birefringence of the wafer, the first quadrant 106a is centered about an axis of birefringence. A first polarimetric spectrum is obtained. The polarizer 102 may then be rotated 90° by a rotating means (not shown) so that the fourth quadrant 106b is now assumed to be centered about the axis of polarization and the first quadrant is covered instead, and a second polarimetric spectrum is obtained. A comparison of the first and second spectra will indicate the presence of any axis or axes of birefringence in the wafer 3. Even where the first and fourth quadrants are not centered about the axis of the polarizer, a comparison of the two spectra may still reveal axis or axes of birefringence.

Figure 6:
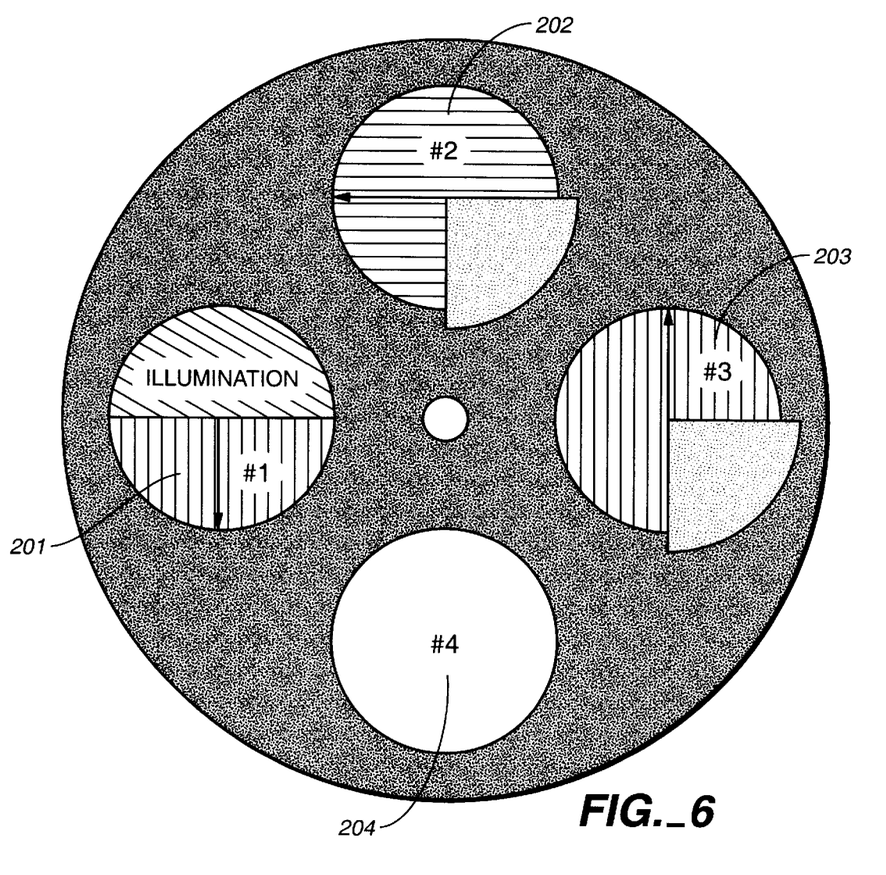
FIG. 6 is a schematic view of a wheel with four different apertures, with three of the apertures having polarizers therein to illustrate the preferred embodiment of the invention.

The above-described method for detecting birefringence of crystals may also be performed using a rotatable wheel 200 shown in FIG. 6. Thus, the polarizer 102 of FIG. 1 may be replaced by wheel 200. In order to perform the measurement described above in reference to FIG. 1 to detect polarimetric parameters, wheel 200 is rotated until the polarizer 201 at position 1 is in the path of the illumination beam passing through the aperture 28 to the beam divider 45. The illumination aperture will consist of the first and fourth quadrants 106a, 106b, and the reflection from the wafer 3 will be collected through an aperture in the second and third quadrants. Where it is desirable to block or cover the first quadrant 106a in FIGS. 4B, 6B, wheel 200 is rotated until polarizer 202 in position 2 is in the path of the radiation beam between aperture mirror 28 and beam divider 45. The illumination aperture will consist only of the fourth quadrant 106b, and the reflection from the wafer 3 will be collected only through aperture 106c in the second quadrant. Where it is desirable to block or cover the fourth quadrant 106b instead, wheel 200 is rotated until the polarizer 203 in position 3 is in the optical path. The illumination aperture will consist only of the first quadrant 106a, and the reflection from the wafer 3 will be collected only through aperture 106d in the third quadrant. Where it is desirable to operate in the same manner as U.S. Pat. No. 5,747,813, wheel 200 is rotated until an aperture 204 in position 4 with no polarizer therein is in the optical path of the beam between aperture mirror 28 and beam divider 45.

While in the embodiments described above, birefringence detection is achieved by using different illumination apertures, essentially the same result can be achieved by using collection apertures instead. In other words, instead of blocking part of the illumination aperture in the path of the illumination radiation beam, part of the collection aperture in the path of radiation reflected from the sample and then collected and directed to the spectrometer and detector may be blocked or covered instead. Such and other variations are within the scope of the invention.

The application using system 8 for detecting birefringence is described above. System 8 can also be used for detecting other parameters of the sample surface. From the equations and the description above in reference to the Figures, especially FIGS. 3A and 3B, the reflected spectrum detected by spectrometer of photodiode array 72 use information concerning Δ, a polarimetric parameter commonly used in ellipsometry and related to thicknesses and refractive indices of thin films at the surface of the sample. Therefore, if certain aspects of the sample surface are known, such known aspects may be combined with the information concerning polarimetric parameters measured by system 8 to derive useful information on the sample, such as film thicknesses and refractive indices.

In the preferred embodiments, the reflected spectrum obtained from photodiode array 72 is compared to the reference spectrum from photodiode array 74 to derive polarimetric parameters, thereby improving signal to noise ratio. For some applications, however, such polarimetric parameters may be derived from the reflected spectrum alone, without the use of a reference spectrum. For such applications, the reference beam 48 is not required, so that all the components associated with the generation of beam 48 and the reference spectrum may be omitted in FIGS. 1 and 2. Such and other variations are within the scope of the invention.

The spectroscopic ellipsometer 300 in the combined instrument of FIG. 1 will now be described. As shown in FIG. 1, a portion of the radiation originating from the xenon arc lamp 10 that has passed through focus 18 and 20 is diverted by a beam splitter 302 to a fiber optic cable 304 which supplies the radiation to a collimator 306. After being collimated, the beam is polarized by polarizer 310 and is focused by focus mirror 312 to the wafer 3. The reflection of such beam is collected by a collection mirror 314 and reflected by folding mirror 316 through an analyzer 320 before it is supplied to spectrometer 322 and detector 324 for detection. The polarizer 310 and analyzer 320 are rotated relative to each other so that the amplitude and phase of the change in polarization state of the beam 308 caused by the reflection at the wafer 3 can be measured. For a more detailed description of the operation of the spectroscopic ellipsometer 300, please see U.S. Pat. No. 5,608,526.

To measure a sample with layers of thin film, it may be desirable to employ a combined instrument, including system 8 for measuring polarimetric parameters and spectroscopic ellipsometer 300, as shown in FIG. 1. System 8 and spectroscopic ellipsometer 300 are arranged so that sample beam 46 and sample beam 308 are focused onto substantially the same spot on the wafer 3. The polarimetric parameters measured by system 8 may then be combined with the ellipsometric parameters measured by system 300 for deriving useful information such as film thicknesses and film refractive indices. The polarimetric parameters obtained by system 8 and the ellipsometric parameters obtained using system 300 may be combined using techniques such as that described in "ANALYSIS OF SEMICONDUCTOR SURFACES WITH VERY THIN NATIVE OXIDE LAYERS BY COMBINED IMMERSION AND MULTIPLE ANGLE OF INCIDENCE ELLIPSOMETRY", Ivan OHLIDAL and Frantisek LUKES, Applied Surface Science 35 (1988–89) 259–273, North Holland, Amsterdam.

Even though the spectral range of spectroscopic ellipsometers does not extend to the deep UV such as about 193 nm, by using the combined instrument, it is possible to accurately measure the indices of refraction at such wavelength. Thus, the combined instrument may be used for measuring the indices of refraction over the combined spectra of the spectroscopic ellipsometer and the polarimeter system 8. By using the combined instrument, and data from both system 8 and from the spectroscopic ellipsometer, the thicknesses and refractive indices of different films of the sample at wavelengths in the spectrum of the spectroscopic ellipsometer can be found. This thickness information may be used together with data from the combined instrument to find the refractive indices of the films in the deep ultraviolet region. The numbers of detectors in the arrays 72, 74 and detector 324 in spectrometer 322 may be chosen to obtain data at the desired wavelengths for optimum results.

In an alternative embodiment, sample beams 46 and 308 need not be focused on the same spot on wafer 3. Wafer 3 may be moved by rotation or linear translation, or a combination of the two motions, in a conventional manner so that spots measured by system 8 are subsequently measured by system 300, or vice versa, and so that data obtained by the two systems measuring the same spot may be combined in the same manner as that described above. Since the rotational and translational of motions are controlled, the relative locations of the spots being measured by the two systems 8 and 300 can be correlated.

While preferably a spectroscopic ellipsometer is combined together with the polarimetric system 8 as described, it is also possible to combine system 8 with a single wavelength ellipsometer. For this purpose, the arrangement in FIG. 1 needs to be modified only slightly by removing the diffractive grating in the optical path of the spectrometer 322, between mirror 321 and detector 324. A laser with wavelength in the polarimetric spectrum may be used as the radiation source for the single wavelength ellipsometer. With the measurements taken by means of the single wavelength ellipsometer and by means of system 8, it is still possible to derive film thicknesses and indices of refraction at wavelengths over the polarimetric spectrum.

While the invention has been described above by reference to various embodiments, it will be understood that changes and modifications may be made without departing from the scope of the invention, which is to be defined only by the appended claims and their equivalents.

What is claimed is:

1. A method for measuring properties of a sample, comprising:

focusing a polarized sample beam of broadband radiation onto the sample, said beam having a multitude of polarization states;

collecting radiation modified by the sample;

analyzing and dispersing the radiation modified by and collected from the sample to provide a polarimetric spectrum, wherein no substantial relative change in polarization state between the radiation and the sample beam is caused by relative motion between optical elements employed in the focusing, collecting and analyzing; and deriving film thickness and refractive index information of the sample from said polarimetric spectrum.

2. The method of claim 1, further comprising splitting a beam of broadband radiation into said polarized sample beam and a reference beam; wherein said focusing focuses said sample beam onto the sample.

3. The method of claim 2, further comprising detecting the reference beam to provide a reference spectrum; and wherein said deriving includes comparing said polarimetric spectrum and said reference spectrum to obtain said film thickness and refractive index information of the sample.

4. The method of claim 3, said beam and said reflected and reference spectra including multiple wavelengths ranging from about 190 nm to about 830 nm.

5. The method of claim 2, said splitting including directing the beam to a mirror placed less than completely across said radiation beam.

6. The method of claim 2, said splitting including deflecting a portion of said beam into a sample beam, the undeflected portion of the radiation defining a reference radiation beam.

7. The method of claim 1, further comprising passing a beam of radiation through a polarizer to obtain the sample beam, wherein said analyzing analyzes by means of an analyzer, and wherein during the focusing and analyzing, the polarizer and analyzer do not rotate.

8. The method of claim 1, further comprising polarizing a beam of broadband radiation to provide said polarized beam, wherein said focusing focuses said polarized beam such that a beam having a multitude of polarization states is focused onto the sample, wherein said polarization states are functions of an angle $\phi$ to a reference plane normal to a sample surface, said angle $\phi$ having a range defining a substantial angle of an illumination aperture.

9. The method of claim 8, wherein said focusing focuses said polarized beam along different planes of incidence onto the sample, said planes being at different angles $\phi$ to the reference plane, the range of said angle of the illumination aperture being about 90 or 180 degrees.

10. The method of claim 1, wherein said focusing and collecting employ a common objective.

11. The method of claim 1, said sample having one or more axes of birefringence, wherein said focusing or collecting employs an aperture centered about one of said axes.

12. The method of claim 11, wherein said focusing and collecting are repeated employing at least two different apertures aligned respectively about at least two of said axes.

13. The method of claim 12, wherein said focusing and collecting are repeated employing at least two different apertures centered respectively about at least two of said axes.

14. The method of claim 1, wherein said focusing and collecting are repeated employing two different apertures to detect presence or absence of an axis of birefringence in the sample.

15. The method of claim 1, said polarimetric spectrum including multiple wavelengths ranging from about 190 nm to about 830 nm.

16. The method of claim 1, wherein said analyzing analyzes the radiation modified by the sample with respect to a predetermined and fixed polarization plane.

17. The method of claim 1, further comprising altering phase of the radiation modified by and collected from the sample prior to analyzing and dispersing it.

18. The method of claim 17, wherein said altering retards said phase of the modified and collected radiation by about $\pi/4$.

19. The method of claim 1, wherein said focusing focuses said sample beam so that it surrounds a line normal to a surface of the sample.

20. An apparatus for measuring properties of a sample, comprising:

first optics focusing a polarized sample beam of broadband radiation onto the surface of the sample, the sample beam having a multitude of polarization states, wherein said sampling beam is focused along directions substantially surrounding a line normal to said sample;

second optics collecting radiation modified by the sample;

an instrument analyzing and dispersing the radiation modified by and collected from the sample to provide a polarimetric spectrum, wherein no substantial relative change in polarization state between the radiation and the sample beam is caused by relative motion between the first and second optics and the instrument; and means for deriving film thickness and refractive index information of the sample from said polarimetric spectrum.

21. The apparatus of claim 20, further comprising:

a radiation source providing a beam of broadband radiation; and third optics splitting said beam of broadband radiation into said polarized sample beam and said reference beam, wherein said first optics focuses said sample beam onto the sample so that the focused beam has a multitude of polarization states, wherein said polarization states are functions of an angle $\phi$ to a reference plane normal to a sample surface, said angle $\phi$ having a range defining a substantial angle of an illumination aperture.

22. The apparatus of claim 21, wherein said first optics focuses said polarized beam along different planes of incidence onto the sample, said planes being at different angles $\phi$ to the reference plane, said angle of the illumination aperture being about 90 or 180 degrees.

23. The apparatus of claim 21, said third optics including a totally reflecting mirror placed less than completely across said beam.

24. The apparatus of claim 21, said third optics deflecting a portion of said radiation in the beam from the source into a sample beam, the undeflected portion of the radiation defining a reference radiation beam.

25. The apparatus of claim 21, wherein said deriving means includes means for comparing said polarimetric spec- 26. The apparatus of cam 25, said radiation beam and said polarimetric and reference spectra including multiple wavelengths ranging from about 190 nm to about 830 nm.

27. The apparatus of claim 21, wherein said third optics includes a polarizing beam splitter.

28. The apparatus of claim 21, wherein said third optics includes a beam divider, said apparatus further including a polarizer.

29. The apparatus of claim 28, said polarizer being in an optical path to the first optics and forms a part of the instrument.

30. The apparatus of claim 28, said polarizer being in an optical path to the first optics, said instrument including an analyzer in an optical path from the second optics.

31. The apparatus of claim 20, said instrument including an analyzer, said apparatus further comprising a polarizer passing a beam of broadband radiation to form said polarizer sample beam, wherein during the focusing by the first optics and analyzing by the instrument, the polarizer and analyzer do not rotate.

32. The apparatus of claim 20, wherein said first and second optics include a common objective that focuses the sample beam onto and collects radiation modified by the sample.

33. The apparatus of claim 20, further comprising a flip-in polarizer and a device moving the polarizer into and out of a path of the beam of broadband radiation from a radiation source to provide the sample beam that is polarized or unpolarized.

34. The apparatus of claim 33, wherein said polarizer polarizes the beam originating from the source and analyses the radiation modified by the sample and collected by the collecting means.

35. The apparatus of claim 20, further comprising a source of radiation, wherein said first optics focuses radiation from the source onto the sample, said sample having one or more axes of birefringence, said apparatus further including at least one aperture aligned with one of said axes, said aperture being in an optical path between the source and the instrument.

36. The apparatus of claim 35, wherein said at least one aperture is centered about said one of the axes.

37. The apparatus of claim 35, further comprising a mechanism selecting one of at least two apertures to be aligned with one of the axes.

38. The apparatus of claim 37, wherein said mechanism causes each of two different apertures to be aligned with a corresponding one of the axes, so that the polarimetric spectra obtained when the two apertures are aligned consecutively with their corresponding axes yields information on birefringence of the sample.

39. The apparatus of claim 38, wherein said mechanism includes a wheel with at least two apertures therein.

40. The apparatus of claim 39, wherein said wheel includes a polarizer in each of the at least two apertures.

41. The apparatus of claim 39, wherein two of said at least two apertures have shapes substantially in the shape of a circle with one quadrant blocked.

42. The apparatus of claim 20, further comprising a source of radiation, wherein said first optics focuses radiation from the source onto the sample, said sample having one or more axes of birefringence, said apparatus further including a mechanism rotating a linear polarizer in an optical path of the sample beam for detecting said axes.

43. The apparatus of claim 20, said broadband radiation including multiple wavelengths ranging from about 190 nm to about 830 nm.

44. The apparatus of claim 20, wherein said instrument analyzes the radiation modified by the sample with respect to a predetermined and fixed polarization plane.

45. The apparatus of claim 20, further comprising a phase retarder in an optical path between the second optics and the instrument, said retarder altering phase of the modified radiation collected from the sample prior to analyzing and dispersing it.

46. The apparatus of claim 45, wherein said retarder retards said phase of the modified and collected radiation by about $\pi/4$.

47. The apparatus of claim 20, said first or second optics including a mirror having a coating that introduces a total change in phase of radiation reflected by it by the first and second optics of about $\pi/2$.

48. The apparatus of claim 20, wherein said sample beam surrounds a line normal to a surface of the sample.

49. A method for obtaining complex refractive index and thickness information of one or more layers of a sample, said method comprising:

focusing a polarized first sample beam of broadband radiation onto the one or more layers, said beam having a multitude of polarization states;

collecting radiation that originates from the first beam and that is modified by the one or more layers of the sample;

analyzing and dispersing the radiation modified and collected from the sample to provide a polarimetric spectrum;

focusing a polarized second beam of radiation at said one or more layers in a direction at an oblique angle to the one or more layers;

obtaining measurements of changes in polarization state in amplitude and phase of the radiation that has been modified by the one or more layers and that originates from the second beam; and determining complex refractive index and thickness information of said one or more layers from said measurements and the polarimetric spectrum.

50. The method of claim 49, wherein said first and second beams of radiation are focused to substantially the same area of said one or more layers.

51. The method of claim 49, wherein said first and second beams of radiation are focused to the one or more layers substantially simultaneously, and said collecting, analyzing and obtaining are performed substantially simultaneously.

52. The method of claim 49, further comprising splitting a beam of broadband radiation into said first beam and a reference beam; wherein said first beam focusing focuses said first beam onto the one or more layers.

53. The method of claim 52, further comprising detecting the reference beam to provide a reference spectrum; and wherein said determining includes comparing said polarimetric spectrum and said reference spectrum.

54. The method of claim 52, said splitting including directing the beam of broadband radiation to a mirror placed less than completely across said radiation beam.

55. The method of claim 52, said splitting including deflecting a portion of said beam of broadband radiation into a sample beam, the undeflected portion of the radiation defining a reference radiation beam.

56. The method of claim 49, further comprising polarizing a beam of broadband radiation to provide a polarized beam, wherein said focusing focuses such polarized beam such that the first polarized sample beam having a multitude of polarization states is focused onto the sample.

57. The method of claim 56, wherein said focusing focuses said polarized beam along different planes of incidence onto the sample.

58. The method of claim 49, wherein said first beam focusing and collecting employ a common objective.

59. The method of claim 49, said polarimetric spectrum including multiple wavelengths ranging from about 190 nm to about 830 nm.

60. The method of claim 49, wherein said analyzing and dispersing analyzes the radiation modified by the sample with respect to a predetermined and fixed polarization plane.

61. The method of claim 49, wherein the second beam focusing focuses a polarized second laser beam at said one or more layers, said obtaining obtains measurements of changes in polarization state caused by the one or more layers at the wavelength of the laser, and said determining determines the refractive indices of the one or more layers over said polarimetric spectrum.

62. The method of claim 49, wherein the second beam focusing focuses a polarized second beam of broadband radiation at said one or more layers, said obtaining obtains measurements of changes in polarization state caused by the one or more layers over a spectrum of the second beam, and said determining determines the refractive indices of the one or more layers over a combined spectrum of the first and second beams.

63. The method of claim 62, said combined spectrum including multiple wavelengths ranging from about 190 nm to about 830 nm.

64. The method of claim 49, further comprising altering phase of the radiation modified by and collected from the sample prior to analyzing and dispersing it.

65. The method of claim 64, wherein said altering retards said phase of the modified and collected radiation by about $\pi/4$.

66. An apparatus for obtaining complex refractive index and thickness information of one or more layers of a sample, said apparatus comprising:
   first optics focusing a first polarized sample beam of broadband radiation to the one or more layers, and a second sample beam of polarized radiation at said one or more layers in a direction at an oblique angle to the one or more layers;
   second optics collecting radiation that originates from the first beam and that is modified by the one or more layers of the sample;
   an instrument analyzing and dispersing the radiation modified and collected from the sample to provide a polarimetric spectrum;
   an ellipsometer obtaining measurements of changes in polarization state in amplitude and phase of the modified radiation from the one or more layers originating from second beam; and
   means for deriving the complex refractive index and thickness information of said one or more layers from the measurements of the ellipsometer and the polarimetric spectrum.

67. The apparatus of claim 66, wherein said first optics focuses the first and second beams of radiation to substantially the same area of said one or more layers.

68. The apparatus of claim 66, wherein said instrument includes a spectrometer.

69. The apparatus of claim 66, wherein said first optics focuses the first and second beams of radiation to the one or more layers substantially simultaneously, and said second optics, the instrument and the ellipsometer perform their respective functions substantially simultaneously.

70. The apparatus of claim 66, further comprising:
   a radiation source providing a beam of broadband radiation; and
   third optics splitting said beam of broadband radiation into said polarized first beam and a reference beam, wherein said first optics focuses said first beam onto the one or more layers of the sample so that the focused beam has a multitude of polarization states.

71. The apparatus of claim 70, wherein said third optics splits said beam from the source into a polarized sample beam and a polarized reference beam.

72. The apparatus of claim 71, said third optics including a totally reflecting mirror placed less than completely across said beam.

73. The apparatus of claim 71, said third optics deflecting a portion of said radiation in the beam from the source into a sample beam, the undeflected portion of the radiation defining a reference radiation beam.

74. The apparatus of claim 71, wherein said third optics includes a polarizing beam splitter.

75. The apparatus of claim 71, wherein said third optics includes a beam divider, said apparatus further including a polarizer.

76. The apparatus of claim 75, said polarizer being in an optical path to the first optics and forms a part of the instrument.

77. The apparatus of claim 75, said polarizer being in an optical path to the first optics, said instrument including an analyzer in an optical path from the second optics.

78. The apparatus of claim 66, further comprising a detector detecting the reference beam to provide a reference spectrum, wherein said deriving means includes means for comparing said polarimetric spectrum and said reference spectrum.

79. The apparatus of claim 78, said polarimetric and reference spectra including multiple wavelengths ranging from about 190 nm to about 830 nm.

80. The apparatus of claim 66, said instrument including an analyzer, said apparatus further comprising a polarizer polarizing a beam of broadband radiation to generate the first polarized sample beam, wherein said analyzer and the polarizer do not rotate when radiation from the first and second beams is modified by the sample and collected, dispersed, analyzed and measured.

81. The apparatus of claim 66, wherein said first optics focuses said polarized beam along different planes of incidence onto the sample.

82. The apparatus of claim 66, wherein said first and second optics include a common objective that focuses the first beam onto and collects radiation modified by the one or more layers at the surface of the sample.

83. The apparatus of claim 66, further comprising a flip-in polarizer and a mechanism moving the polarizer into and out of a path of a beam of broadband radiation from a radiation source to provide the first sample beam that is focused by the first optics.

84. The apparatus of claim 83, wherein said polarizer polarizes the beam originating from the source to provide the first sample beam and analyses the radiation that is modified by the sample and collected by the second optics and that originates from the first beam.

85. The apparatus of claim 66, said broadband radiation of the first and second beams including multiple wavelengths ranging from about 190 nm to about 830 nm.

86. The apparatus of claim 66, wherein said instrument analyzes the radiation modified by the surface of the sample and from the first sample beam with respect to a predetermined and fixed polarization plane.

87. The apparatus of claim 66, wherein said second beam is a laser beam whose wavelength is in the polarimetric spectrum, wherein the ellipsometer is a single wavelength ellipsometer that obtains measurements of changes in polarization state caused by the one or more layers at the wavelength of the laser, and said deriving means derives the thickness information and refractive indices over said polarimetric spectrum.

88. The apparatus of claim 66, said second beam having wavelengths in a broadband, wherein the ellipsometer is a spectroscopic ellipsometer that obtains measurements of changes in polarization state caused by the one or more layers over the spectrum of the second beam, and said determining determines the refractive indices of the one or more layers over a combined spectrum of the first and second beams.

89. The method of claim 88, said combined spectrum including multiple wavelengths ranging from about 190 nm to about 830 nm.

90. The apparatus of claim 66, said first or second optics including a mirror having a coating that introduces a total change in phase of radiation reflected by it by the first and second optics of about $\pi/2$.

* * * * *